US008251901B2

(12) United States Patent
White et al.

(10) Patent No.: US 8,251,901 B2
(45) Date of Patent: Aug. 28, 2012

(54) RETRACTOR FOR MINIMALLY INVASIVE SURGERY

(75) Inventors: Patrick Michel White, West Chester, PA (US); Thomas Zehnder, Bäch (CH); Reto Braunschweiler, Noftenbach (CH)

(73) Assignee: Greatbatch Medical S.A., Orvin (CH)

( * ) Notice: Subject to any disclaimer, the term of this patent is extended or adjusted under 35 U.S.C. 154(b) by 779 days.

(21) Appl. No.: 12/247,297

(22) Filed: Oct. 8, 2008

(65) Prior Publication Data

US 2009/0131755 A1  May 21, 2009

Related U.S. Application Data

(60) Provisional application No. 60/978,147, filed on Oct. 8, 2007.

(51) Int. Cl.
*A61B 1/32* (2006.01)

(52) U.S. Cl. .................................. 600/210; 606/279

(58) Field of Classification Search .................. 600/201, 600/204, 210, 211, 235; 606/246, 263, 279, 606/99, 103, 104, 86 A
See application file for complete search history.

(56) References Cited

U.S. PATENT DOCUMENTS

| 4,805,602 A * | 2/1989 | Puno et al. ............... 606/267 |
| 2007/0106123 A1 | 5/2007 | Gorek et al. |
| 2008/0161857 A1* | 7/2008 | Hestad et al. ............. 606/264 |

* cited by examiner

*Primary Examiner* — Alvin Stewart
*Assistant Examiner* — David Comstock
(74) *Attorney, Agent, or Firm* — Michael F. Scalise

(57) ABSTRACT

A surgical retractor comprises an elongate member having a coupling region disposed at one end thereof. The retractor is adapted to engage a base of a head of a pedicle screw. The coupling region of the elongate member has a filament-receiving hole adapted to receive a filament which captures the head of the pedicle screw. During surgery, a physician may retract muscle and soft tissue by simply pressing the elongate member against such tissue.

20 Claims, 5 Drawing Sheets

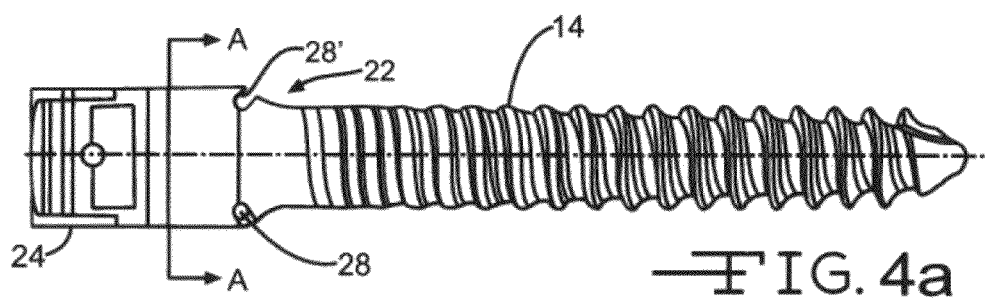
FIG. 4a
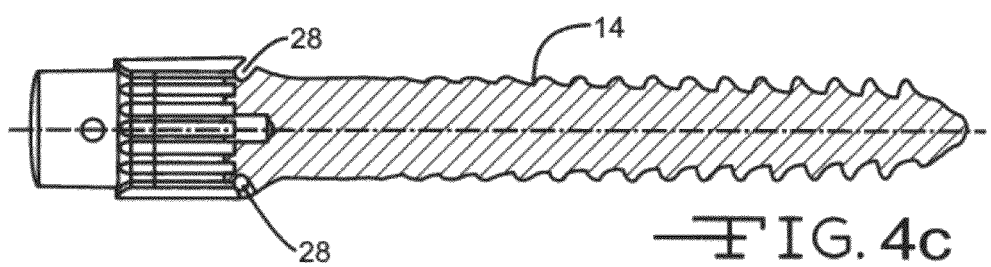
FIG. 4c
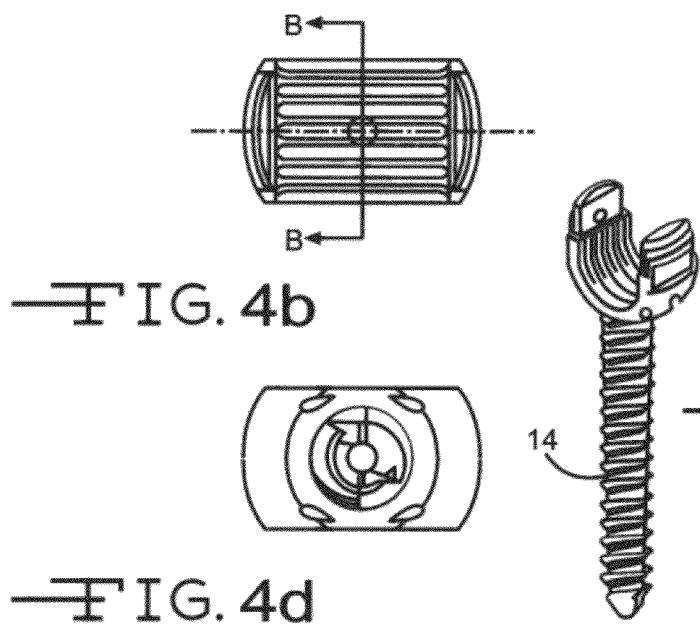
FIG. 4b
FIG. 4e
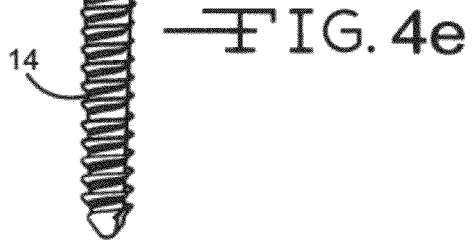
FIG. 4d

RETRACTOR FOR MINIMALLY INVASIVE SURGERY

CROSS REFERENCE TO RELATED APPLICATIONS

This application claims the benefit of U.S. Provisional Patent Application No. 60/978,147 filed Oct. 8, 2007.

BACKGROUND OF THE INVENTION

This invention relates to surgical retractors and in particular, surgical retractors which retract muscle and soft tissue from an operative site during spinal surgery and the installation of spinal prosthesis.

Nothing herein is to be construed as an admission that the present invention is not entitled to antedate such material by virtue of prior invention.

US Patent Application Publication US 2007/0106123A1, to Gorek et al, filed Sep. 26, 2006, the content of which are incorporated herein by reference thereto and relied upon, describes such a retractor. Although suitable for minimally invasive surgery, the Gorek device suffers from the need for special tools to remove the retractor elongate members or blades 8.

What is needed is a retractor and method suitable for minimally invasive surgery which does not require special tools and which is otherwise easy to remove after it's purposes are served.

SUMMARY OF THE INVENTION

The retractor assembly of the invention includes an elongate member, a pedicle screw, and a filament. The elongate member has a coupling region disposed at one end thereof. The retractor assembly is adapted to engage a base of a head of the pedicle screw. The coupling region of the elongate member has a filament-receiving hole adapted to receive the filament which captures the head of the pedicle screw, following a path or alternate path to loop around the pedicle screw at the base of the head. The filament has a free end which may be wedged in a filament receiving slit, to fix the free end in place.

An object of the invention is to better enable minimally invasive surgery while providing a simple means to remove the retractors, by simply removing the free ends of the wire from their retainer and pulling them through the filament receiving recesses.

BRIEF DESCRIPTION OF THE DRAWINGS

FIG. 4a is a side view of a pedicle screw for use with the retractor assembly of the invention.

FIG. 4b is a cross sectional view of the pedicle screw taken along plane A-A of FIG. 4a.

FIG. 4c is a cross sectional view of the pedicle screw taken along plane B-B of FIG. 4b.

FIG. 4d is a rear view of the pedicle screw for use with the retractor assembly of the invention.

FIG. 4e is a perspective view of the pedicle screw for use with the retractor assembly of the invention.

DETAILED DESCRIPTION OF THE PREFERRED EMBODIMENT

Figure 1A:
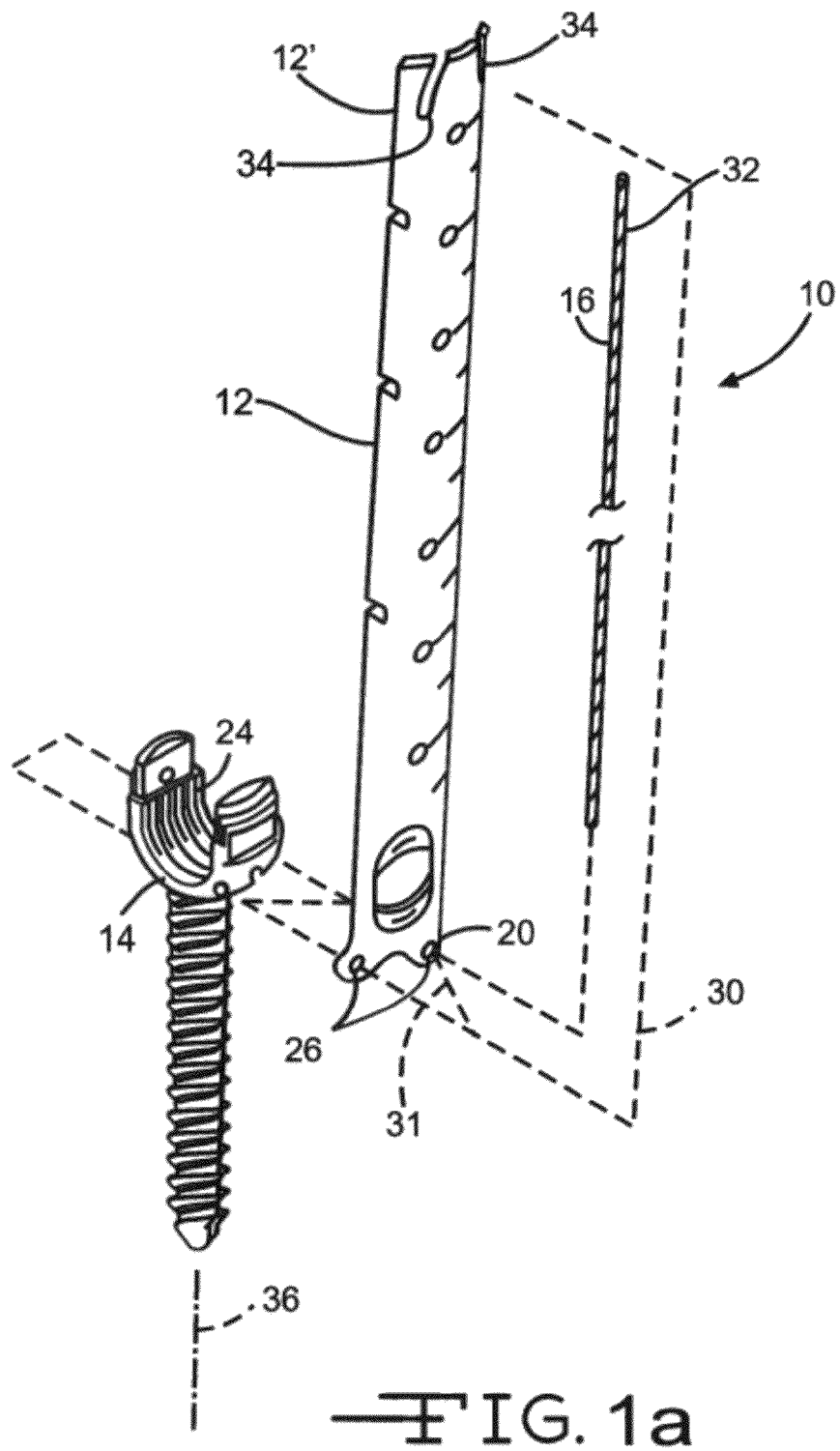
FIG. 1a is an exploded view of the retractor assembly of the invention.

Referring now to FIG. 1a, the retractor assembly 10 of the invention includes an elongate member 12, a pedicle screw 14 and a filament 16. The elongate member 12 has a coupling region 20 disposed at one end thereof. The retractor assembly 10 is adapted to engage a base 22 of a head 24 of the pedicle screw 14. The coupling region 20 of the elongate member 12 has a filament-receiving hole 26 adapted to receive the filament 16 which captures the head 24 of the pedicle screw 14, following a path 30 or alternate path 31 to loop around the pedicle screw 14 at the base 22 of the head 24. The filament 16 has a free end 32 which may be wedged in a filament receiving slit 34, to fix the free end in place.

The elongate member 12 may be made of a polymer, as also the filament 16.

Figure 1B:
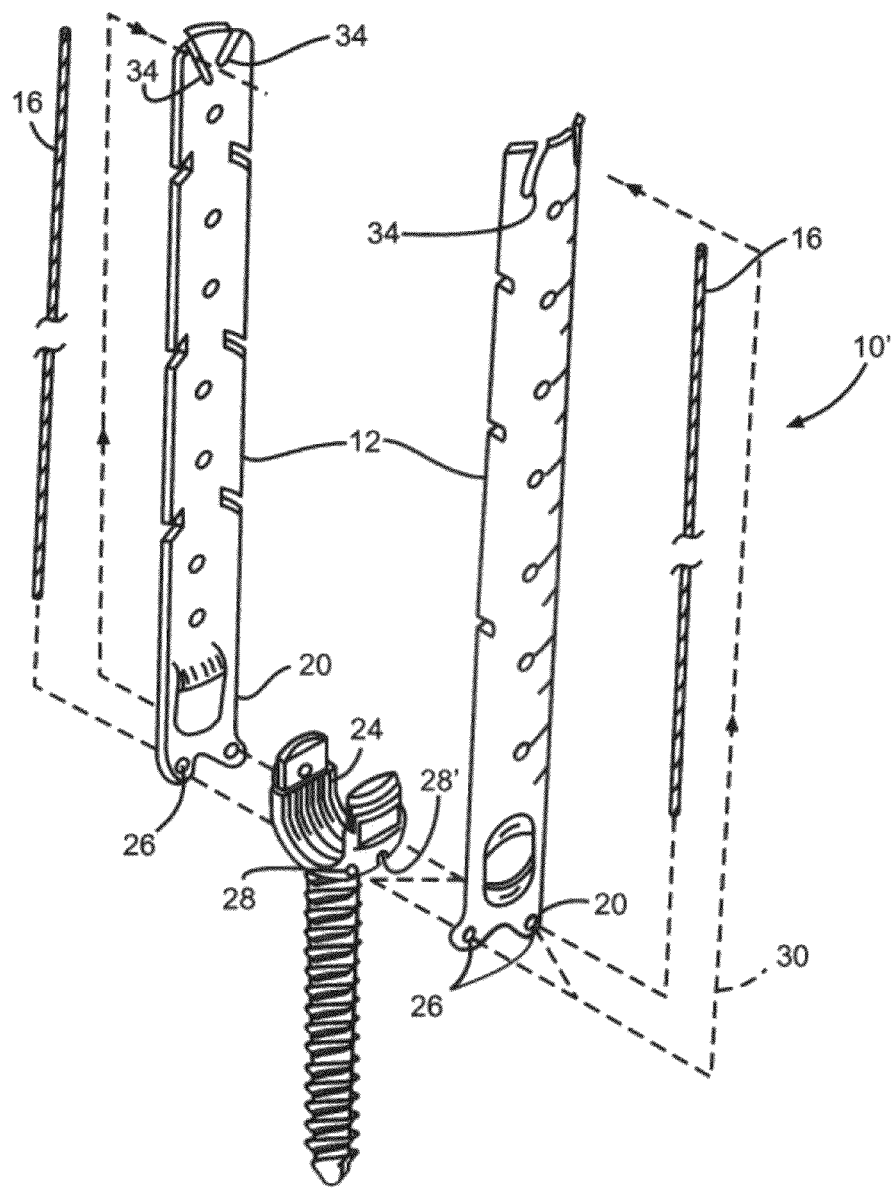
FIG. 1b is an exploded view of another embodiment of the retractor assembly of the invention.

Referring now to FIG. 1b, in an alternate embodiment, a retractor assembly 10' includes two elongate members 12 and filaments 16 which pass through filament receiving holes 28 or recesses 28' (see FIG. 4a) at the base 22 of the head 24 of the pedicle screw 14. Alternatively, the filaments 16 may simply loop around the base 22 of the head 24 as shown in FIG. 1a.

During surgery, a physician may retract muscle and soft tissue by simply pressing the elongate member against such tissue. Further, to remove the assembly, all that is required, is that the filament ends 32 be removed from their holders and the filaments pulled out of the assembly. No special tools are therefore required for removal after installation of the pedicle screw 14 and rod (not shown) which interfaces with the pedicle screw.

Figure 2:
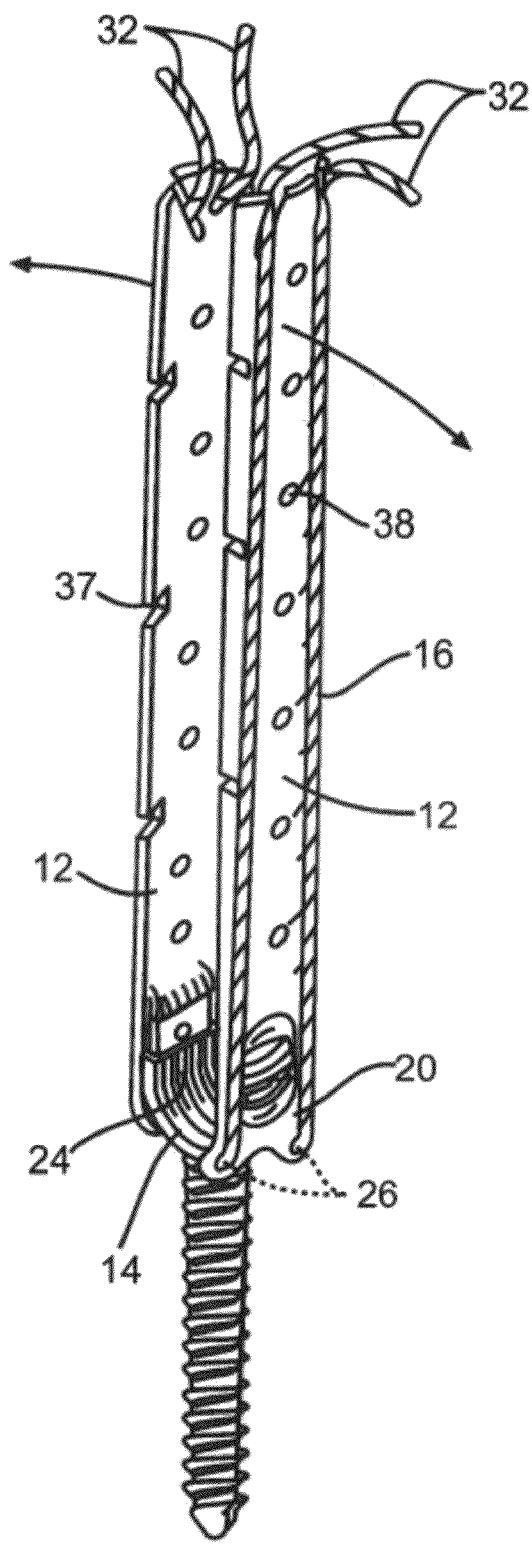
FIG. 2 is a perspective view of the retractor assembly of the invention.
Figure 3:
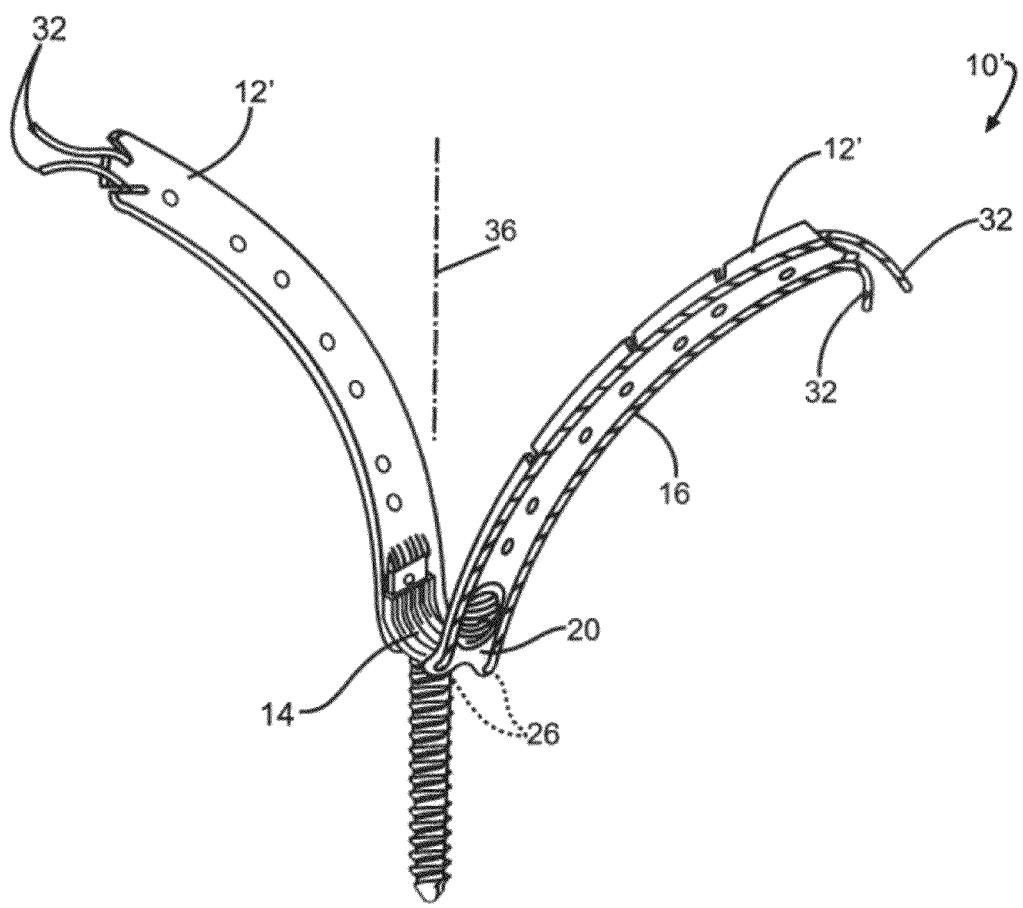
FIG. 3 is a perspective view of the retractor assembly of the invention, retracted to push back tissue from the operative site.

Referring now FIG. 2, the retractor assembly 10' of the invention is shown in a non-extended, assembled position. To retract tissue, a distal end 12' of an elongate member 12 must be moved away (see FIG. 3) from the axis 36 of the assembly 10', and so, like a tongue depressor, it moves tissue out of the way so a surgeon can gain functional access to the operative site.

A method of performing spine surgery using the invention 10, 10', includes the following steps. In a first step, at least two retractor assemblies 10, 10', are provided to the surgical site, each retractor assembly including at least one elongate member attached to a coupling region of the retractor wherein filaments passing through the retractor assemblies and around the base of the head of the pedicle screw retain the retractor assemblies about the screw. In a second step, a first screw is secured to a portion of a first vertebral body. In a third step, tissue is retracted using the at least one elongate member of the first retractor. In a fourth step, a second screw is secured to a portion of a second vertebral body. In a fifth step, tissue is retracted using the at least one elongate member of the second retractor. In a sixth step, a rod is inserted between the first and second screws. In a seventh step, the rod is secured to the first and second screws. In an eighth step, the first and second retractors are removed by removing the filament 16 in a conventional manner such as by cutting.

In an advantage, the assembly 10, 10' enables minimally invasive surgery while providing a simple means to remove the retractors, by simply removing the free ends 32 of the wire from their retainer 34 and pulling them through the filament receiving recesses 26, 26'.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the claims which ultimately issue in this application.

What is claimed is:

1. A surgical retractor, comprising:
   a) at least one elongate member comprising a sidewall having a length extending from a distal portion to a spaced apart proximal portion, wherein the proximal portion comprises a coupling opening bounded by material of the elongate member and at least one filament-receiving hole therein; and
   b) a filament,
   c) wherein the elongate member is detachably connectable to a head of a pedicle screw at the coupling opening with the filament being receivable in the filament-receiving hole and loopable around the screw to thereby connect the elongate member to the pedicle screw.

2. The surgical retractor of claim 1 wherein the filament is loopable through the filament-receiving hole so as to cinch around the base of the head of the pedicle screw.

3. The surgical retractor of claim 1 or 2 wherein the distal portion of the elongate member has at least one slit adapted to receive an end of the filament to thereby fix the filament in place.

4. The surgical retractor of claim 1 wherein the elongate member has at least two filament receiving holes.

5. The surgical retractor of claim 1 wherein the distal portion of the elongate member has at least one filament receiving slit.

6. The surgical retractor of claim 1 wherein the elongate member is made from a polymer.

7. The surgical retractor of claim 1 wherein the filament is made from a polymer.

8. A method of performing spine surgery, comprising the steps of
   a) providing:
      i) at least two pedicle screws, each screw comprising a head supported on a threaded section;
      ii) at least a first and a second retractor assemblies, the first retractor assembly including at least a first elongate member and a first filament and the second retractor assembly including at least a second elongate member and a second filament, wherein each of the elongate members comprises a sidewall having a length extending from a distal portion to a spaced apart proximal portion with the proximal portion comprising a coupling opening bounded by material of the elongate member and at least one filament-receiving hole therein; and
      iii) wherein each of the elongate members is detachably connectable to a screw head at its coupling opening with the filament being receivable in the filament-receiving hole and loopable around the screw to thereby connect the elongate member to the pedicle screw;
   b) securing a first screw to a first vertebral body;
   c) retracting tissue by connecting the coupling opening of the first elongate member of the first retractor assembly to the first screw head with the filament received in the filament-receiving hole and looped around the first screw to thereby connect the first elongate member to the first pedicle screw and then moving the distal portion of the first elongate member in a lateral direction away from an imaginary extension of a first longitudinal axis of the first pedicle screw;
   d) securing a second screw to a second vertebral body;
   e) retracting tissue by connecting the coupling opening of the second elongate member of the second retractor assembly to the second screw head with the filament received in the filament-receiving hole and looped around the second screw to thereby connect the second elongate member to the second pedicle screw and then moving the distal portion of the second elongate member in a lateral direction away from an imaginary extension of a second longitudinal axis of the second pedicle screw;
   f) inserting a rod between the first and second screws;
   g) securing the rod to the first and second screws; and
   h) removing the first and second retractors by removing the respective first and second filaments from being looped around the first and second screws.

9. A surgical retractor system, which comprises:
   a) a pedicle screw comprising a head supported on a threaded section;
   b) at least one elongate member comprising a sidewall having a length extending from a distal portion to a spaced apart proximal portion, wherein the proximal portion comprises a coupling opening bounded by material of the elongate member and at least one filament-receiving hole therein; and
   c) a filament,
   d) wherein the elongate member is detachably connectable to the screw head at the coupling opening with the filament being receivable in the filament-receiving hole and loopable around the screw to thereby connect the elongate member to the pedicle screw.

10. The surgical retractor system of claim 9 wherein the pedicle screw has at least one filament-receiving hole or recess for receiving the filament to thereby fix the elongate member to the screw.

11. The surgical retractor system of claim 9 wherein the head of the pedicle screw comprises a structure that is received in the coupling opening when the elongate member is connected to the pedicle screw.

12. The surgical retractor of claim 9 wherein the distal portion of the elongate member has at least one slit adapted to receive an end of the filament.

13. The surgical retractor of claim 9 wherein the elongate member has at least two filament receiving holes.

14. The surgical retractor of claim 9 wherein the elongate member is made from a polymer.

15. The surgical retractor of claim 9 wherein the filament is made from a polymer.

16. A surgical retractor system, which comprises:
a) a pedicle screw comprising a head supported on a threaded section;
b) two elongate members, each one comprising a sidewall having a length extending from a distal portion to a spaced apart proximal portion, wherein the proximal portion comprises a coupling opening bounded by material of the elongate member and at least one filament-receiving hole therein; and
c) a filament,
d) wherein the elongate members are detachably connectable to spaced apart locations on the screw head at their coupling openings with the filament being receivable in the filament-receiving holes and loopable around the screw to thereby connect the spaced apart elongate members to the pedicle screw.

17. The surgical retractor system of claim 16 wherein the head of the pedicle screw comprises two diametrically opposed structures that are received in the coupling openings when the two elongate members are connected to the pedicle screw.

18. The surgical retractor system of claim 16 wherein the pedicle screw has at least one filament-receiving hole or recess for receiving the filament to thereby fix the elongate member to the screw.

19. The surgical retractor system of claim 16 wherein the distal portion of the elongate member has at least one slit adapted to receive an end of the filament.

20. The surgical retractor system of claim 16 wherein both the elongate member and the pedicle screw have two filament-receiving holes that align with each other when the elongate member is supported on the screw.

\* \* \* \* \*